US010365237B2

(12) United States Patent
Mohebbi et al.

(10) Patent No.: US 10,365,237 B2
(45) Date of Patent: Jul. 30, 2019

(54) NMR SENSOR DEVICE FOR THE ANALYSIS OF FLUID DISTRIBUTION IN ABSORBENT ARTICLES

(71) Applicant: The Procter & Gamble Company, Cincinnati, OH (US)

(72) Inventors: Behzad Mohebbi, Schwallbach am Taunus (DE); Jan Claussen, Wiesbaden (DE); Justyna Paradowska, Frankfurt am Main (DE); J Michael Bills, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 80 days.

(21) Appl. No.: 15/729,703

(22) Filed: Oct. 11, 2017

(65) Prior Publication Data

US 2018/0106738 A1    Apr. 19, 2018

Related U.S. Application Data

(60) Provisional application No. 62/408,114, filed on Oct. 14, 2016.

(51) Int. Cl.
*G01N 24/08* (2006.01)
*G01R 33/30* (2006.01)
(Continued)

(52) U.S. Cl.
CPC ........... *G01N 24/082* (2013.01); *A61F 13/42* (2013.01); *A61F 13/84* (2013.01); *G01N 24/08* (2013.01);
(Continued)

(58) Field of Classification Search
USPC .................................................. 324/300–322
See application file for complete search history.

(56) References Cited

U.S. PATENT DOCUMENTS

| 7,358,734 B2 | 4/2008 | Blümich et al. |
| 7,391,215 B2 | 6/2008 | Callaghan et al. |

(Continued)

OTHER PUBLICATIONS

Oligschläger, D., et al., Miniature mobile NMR sensors for material testing and moisture-monitoring, diffusion-fundamentals.org—The Open-Access Journal for the Basic Principles of Diffusion Theory, Experiment and Application, vol. 22(8), pp. 1-25 (2014).

(Continued)

*Primary Examiner* — Jay Patidar
(74) *Attorney, Agent, or Firm* — Andrew J. Hagerty; Sara M. DeCristofaro

(57) ABSTRACT

A device for the analysis of fluid distribution in an absorbent article is disclosed. The device provides for a frame, a pressure chamber disposed in contacting and mating engagement with the frame, and a NMR sensor in cooperative engagement with the frame and the pressure chamber. The pressure chamber further comprises a top plate and a conformable surface. The absorbent article is disposable between the top plate and the conformable surface. The NMR sensor is disposable proximate to the pressure chamber and is capable of measuring a fluid distribution in the absorbent article when the absorbent article is disposed between the top plate and the conformable surface of the pressure chamber and the NMR sensor is disposed proximate to a surface of the absorbent article.

7 Claims, 17 Drawing Sheets

(51) Int. Cl.
A61F 13/84 (2006.01)
G01R 33/561 (2006.01)
A61F 13/42 (2006.01)

(52) U.S. Cl.
CPC ......... *G01R 33/30* (2013.01); *G01R 33/5617* (2013.01); *A61F 2013/8488* (2013.01); *G01R 33/305* (2013.01)

(56) References Cited

U.S. PATENT DOCUMENTS

| | | | |
|---|---|---|---|
| 9,964,501 B2* | 5/2018 | Taicher | G01N 24/08 |
| 2011/0050223 A1* | 3/2011 | Balcom | G01R 33/305 |
| | | | 324/307 |
| 2013/0307543 A1* | 11/2013 | Endo | G01R 33/307 |
| | | | 324/321 |
| 2015/0130463 A1* | 5/2015 | Wellman | G01N 24/08 |
| | | | 324/321 |

OTHER PUBLICATIONS

Oligschläger, D., et al., Moisture dynamics in wall paintings monitored by single-sided NMR, Magnetic Resonance in Chemistry (MRC), vol. 53, pp. 48-57 (2015).

Vuong, Q. L., et al., Paramagnetic nanoparticles at potential MRI contrast agents: characterization, NMR relaxation, simulations and theory, Magnetic Resonance Mater Phy, vol. 25, pp. 467-478 (2012).

* cited by examiner

NMR SENSOR DEVICE FOR THE ANALYSIS OF FLUID DISTRIBUTION IN ABSORBENT ARTICLES

FIELD OF THE INVENTION

The present disclosure generally relates to equipment suitable for analyzing the two- and three-dimensional distribution and the kinetics of fluid redistribution in absorbent articles and components thereof. More particularly, the present disclosure relates to a device incorporating a nuclear magnetic resonance (NMR) apparatus that can measure and analyze at least a two-dimensional profile of the fluid distribution in an absorbent article such as a diaper or a catamenial device as well as the components forming such absorbent articles.

BACKGROUND OF THE INVENTION

The liquid distribution and the kinetics of liquid redistribution is vital information that can be used to compare the functionality of different absorbent articles, such as hygiene products, and to develop new products. Currently, several techniques such as X-Ray and MRI are utilized to characterize the 3D liquid distribution within hygiene products. However, there is currently no known process to provide a fast data acquisition process in combination with a high resolution process at low cost to follow the kinetics of fluid movement inside absorbent articles.

NMR is a physical phenomenon based on the principle of exciting nuclear spins with radiofrequency pulses, the frequency of which matches the Larmor frequency of the nuclear spins. In other words, NMR is based on the nuclear magnetic properties of certain elements and isotopes of those elements. It is based on the principle that nuclei with a non-zero spin will have a magnetic dipole and therefore will interact with electromagnetic (EM) radiation.

This principle has been applied in many different research fields such as chemical structure analysis, materials testing and in medicine. To access certain nuclear spins via radiofrequency pulses, the nuclei have to be exposed to a magnetic field. These magnetic fields can be classified as high and low. Low magnetic fields as created by permanent magnets can yield magnetic field strengths up to 85 MHz proton Larmor frequency, whereas superconducting high field magnets reach drastically higher field strengths. Magnetic fields can either be produced by electrical currents running through cryogenically cooled coils of superconducting wires without resistance or by the use of permanent magnets.

The presence or absence of a spin and the nature of this spin is expressed in terms of the spin quantum number of the nucleus, which may either be 0, ½ or multiples of ½. In a uniform magnetic field a nucleus having a spin quantum number of ½ may assume two orientations relative to the applied magnetic field. The two orientations have different energies so that it is possible to induce a nuclear transition by the application of electromagnetic radiation of the appropriate frequency. This transition is resonance. Resonance arises when the correct combination of magnetic field strength and exciting frequency characteristics of the nuclei of interest are applied.

After resonance is achieved the NMR instrument records a signal, the signal being a function of the nature and amount of excited nuclei within the test sample as well as nuclear magnetic relaxation considerations. A NMR device generally comprises one or more magnets producing a strong homogenous field in combination with gradients within a test region to be applied for imaging, spectroscopy or relaxometry. The size and complexity of NMR spectrometers are largely a function of the magnetic field requirements. In contrast to NMR applications requiring homogeneous magnetic fields, single sided, or open, NMR devices make use of inhomogeneous magnetic fields having highly uniform gradients.

One particular early form of single sided NMR, the NMR-Mobile Universal Surface Explorer (NMR-MOUSE) was introduced in 1995. The early design of the NMR-MOUSE was limited to a maximum penetration depth of less than 5 mm, and a depth profile resolution of only about a millimeter due to its U-Shape formed magnet. To achieve a flat, sensitive NMR volume at a greater distance removed from the magnet surface with a higher depth resolution a new magnet design was developed.

The new magnet design provided a magnetic assembly for an NMR apparatus, including a plurality of primary permanent magnets disposed in an array about an axis (hereafter "longitudinal axis"), the arrangement and/or characteristics of the plurality of magnets being such so as to create a zone of homogeneous magnetic field at some location along the axis forward of the array (and into the material when provided). The assembly can include a secondary permanent magnet located along the longitudinal axis, at least partly within the array of primary magnets.

As shown in FIG. 1, an exemplary prior art NMR-MOUSE 1005 provides a portable open NMR sensor equipped with a permanent magnet geometry that generates a highly uniform gradient perpendicular to the scanner surface. A frame 1007 with horizontal plane 1006 supports the specimen and remains stationary during the test. A flat sensitive volume of the specimen is excited and detected by a surface RF coil 1012 placed on top of the magnet 1010 at a position that defines the maximum penetration depth into the specimen. By repositioning the sensitive slice across the specimen by means of a high precision lift 1008, the scanner can produce one-dimensional profiles of the specimen's structure with high spatial resolution. If necessary the depth can be adjusted using the spacer 1011.

FIG. 2 shows an exemplary absorbent article specimen 1000 prepared for use with the exemplary prior art NMR-MOUSE 1005. The garment facing side of the specimen 1003 is mounted on a 50 mm×50 mm×0.30 mm glass slide 1001 using a 40.0 mm by 40.0 mm piece of double-sided tape 1002 (tape must be suitable to provide NMR signal amplitude). A top cap 1004 is prepared by adhering two 50 mm×50 mm×0.30 mm glass slides 1001 together using a 40 mm by 40 mm piece of two-sided tape 1002. The cap is then placed on top of the specimen. The two tape layers are used as functional markers to define the dimension of the specimen by the instrument. As can be understood, the prior art absorbent article system does not easily allow for the analysis of absorbent articles that expand. Additionally, a typical RF pulse sequence used in prior art NMR devices, such as the NMR-MOUSE system, is the Carr-Purcell-Meiboom-Gill (CPMG) pulse train. A pulse sequence is a visual representation of the pulses and delays used in a NMR experiment. A pulse is a collection of oscillating waves with a broad range of frequencies used to rotate the bulk magnetization. Most pulse sequences have more than one pulse which can help for signal enhancement and measuring relaxation times by separation of NMR interactions.

One of skill in the art will recognize that the deterioration of an NMR signal is analyzed in terms of two separate processes, each with their own time constants. One process, associated with $T_1$, is responsible for the loss of signal intensity. The other process, associated with $T_2$, is responsible for the broadening of the signal. Two distinguishable relaxation times in NMR are the longitudinal relaxation with a characteristic time $T_1$, which is also known as Spin-Lattice relaxation, and transverse relaxation with a characteristic time $T_2$, which is also known as Spin-Spin relaxation. The longitudinal relaxation is the time needed for magnetization in z direction to build up and reach an equilibrium state again ($M_{eq}$). The build-up rate of magnetization in z direction is proportional to its deviation from the thermal equilibrium state. Transverse relaxation corresponds to the loss of magnetization in the transverse plan. Stated more formally, $T_1$ is the time constant for the physical processes responsible for the relaxation of the components of the nuclear spin magnetization vector M parallel to the external magnetic field, $B_0$ (which is conventionally oriented along the z axis). $T_2$ relaxation affects the components of M perpendicular to $B_0$. In conventional NMR spectroscopy $T_1$ determines the recycle time, the rate at which an NMR spectrum can be acquired. Values of $T_1$ range from milliseconds to several seconds.

Due to the inhomogeneous static field generated by the open geometry of the profile NMR MOUSE, the free induction decay (FID) (i.e., the observable NMR signal generated by non-equilibrium nuclear spin magnetization precessing about the magnetic field) is too short and not detectable. In order to overcome this problem the CPMG pulse sequence is the most frequently used with single-sided NMR. The CPMG pulse sequence generally consists of a 90° pulse followed by 180° pulses that create a train of spin echoes. This sequence acts to refocus, or regain signal loss due to $B_0$ field inhomogeneity. The initial amplitude of the decay can be related to spin density, while the effective relaxation time $T_{2,eff}$ can be extracted by fitting an exponential function to the signal decay.

An exemplary prior art NMR-MOUSE is the Profile NMR-MOUSE model PM25 with High-Precision Lift available from Magritek Inc., San Diego, Calif. Exemplary requirements for the NMR-MOUSE are a nominal 50-100 µm resolution in the z-direction, a measuring frequency of 13.5 MHz, a maximum measuring depth of 25 mm, a static gradient of 8 T/m, and a sensitive volume (x-y dimension) of 40 mm by 40 mm.

However, several problems exist with the prior art NMR-MOUSE device as would relate to the quantification of two- and three-dimensional distribution, and the kinetics of fluid redistribution associated with absorbent articles and the components thereof. First, it was found that the prior art NMR-MOUSE systems that use current, published CPMG pulse sequences cannot be used for the fast quantification of fluid distribution or fluid movement inside an absorbent article (e.g., diapers and catamenials) as the relaxation times $T_1$ and $T_2$ are strongly dependent upon the characteristics of the absorbent article and the components thereof (such as foams, super absorber, pulp, nonwovens, etc.) and their respective saturation levels. To enable the quantification of liquids in absorbent articles and the components thereof, CPMG pulse sequences that can make the $T_1$ and $T_2$ times independent of the absorbent articles and the components thereof and their relative saturation levels that can enable the fast quantification of liquids inside absorbent articles and components thereof is required.

Second, the current NMR-MOUSE equipment is not suitable for measuring absorbent articles that have, or exhibit, expansive properties. For example, a typical absorbent article such as a diaper, will expand (i.e., swell) when an insult is applied to the surface and the insult migrates inward and is absorbed and/or retained by the constituents forming the absorbent article. This is similar to the observed swelling of a sponge when the surface is insulted by a fluid. The fluid migrates into the sponge and the sponge swells. Swelling causes an absorbent article and the material therein to expand upward (i.e., away from the zone of NMR measurement). Thus, the moisture composition of the portion of the absorbent article disposed inside the static sensitive volume changes. Swelling of an absorbent article due to fluid absorption can have two net effects on NMR measurements regardless of the position chosen. First, the local density is reduced (since the quantity of fluid inside the swelling material is reduced by the same factor as the swelling factor and following swelling kinetics), while at the same time fluid that was already past the sensitive volume can re-enter it from below. This results in potentially confounding factors in the interpretation of kinetic measurements when the absorbent article swelling rate and its effect cannot be determined by a parallel independent NMR test. When measuring the characteristics of swellable objects, such as absorbent articles (diapers, catamenials, etc.) the expansion of the object and ensuing migration of the insulted surface away from the surface of the NMR prevents the observation and analysis of fluid migration into the absorbent article as point of reference (e.g., the insulted surface) having the fluid disposed thereon migrates away from the NMR surface.

Therefore, a need exists and it would be beneficial to provide a new device that can enhance the ability of low-field NMR devices to measure, analyze, and evaluate the migration of fluids into an absorbent article by maintaining the point of reference at a fixed location relative to the NMR. Such a device can improve the ability to map fluid migration through an absorbent article necessary to enhance the development of better quality absorbent articles as well as the materials used to manufacture absorbent articles.

SUMMARY OF THE INVENTION

The present disclosure provides for a device for the analysis of fluid distribution in an absorbent article. The device comprises a frame, a pressure chamber disposed in contacting and mating engagement with the frame, and a NMR sensor in cooperative engagement with the frame and the pressure chamber. The pressure chamber further comprises a top plate and a conformable surface. The absorbent article is disposable between the top plate and the conformable surface. The NMR sensor is disposable proximate to the pressure chamber and is capable of measuring a fluid distribution in the absorbent article when the absorbent article is disposed between the top plate and the conformable surface of the pressure chamber and the NMR sensor is disposed proximate to a surface of the absorbent article.

The present disclosure also provides for a device for the analysis of fluid distribution in an absorbent article. The device comprises a frame capable of having and absorbent article attached thereto and a NMR sensor in cooperative engagement with the frame. The NMR sensor is disposable proximate to the absorbent article. The NMR sensor is capable of measuring a fluid distribution in the absorbent article when said NMR sensor is disposed proximate to a surface of the absorbent article.

DETAILED DESCRIPTION

As used herein, the term "machine direction" (MD) refers to that direction which is parallel to the flow of the component materials used for the formation of absorbent articles through manufacturing equipment. The "cross-machine direction" (CD) is perpendicular to and co-planar with the machine direction. The "Z-direction" refers to that direction that is orthogonal to both the MD and CD. As used herein, the term MD corresponds with the term "y-axis." As used herein, the term CD corresponds with the term "x-axis." As used herein, the term Z-direction corresponds with the term "z-axis."

As used herein, an "absorbent article" or "absorbent articles" refers to articles that absorb any type of fluid. These articles are typically disposable and generally includes paper towels, wipes, toilet paper, facial tissue, absorbent hygienic articles such as diapers and catamenial devices, absorbent articles used in the medical field such as wound dressings and surgical articles, absorbent articles used in food technology and conservation (such as fluid pads for meat, fish and the like), absorbent articles used industrially to absorb fluids, for example to contain spillage of chemicals in fluid form and absorbent hygienic articles, as well as the components of such exemplary absorbent articles which in and of themselves may also be absorbent.

Figure 1:
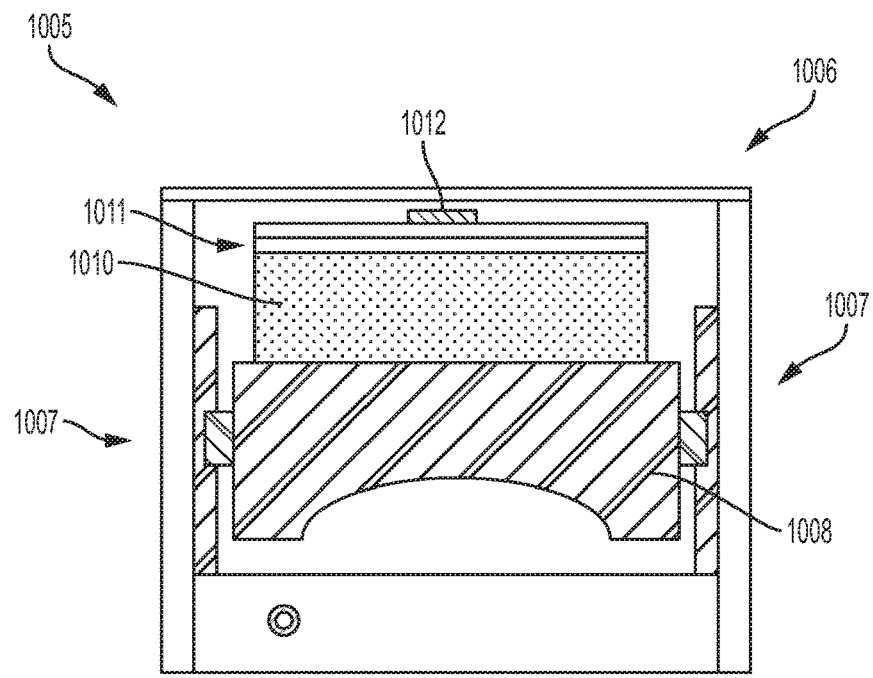
FIG. 1 is a cross-sectional view of an exemplary prior art NMR-MOUSE apparatus.
Figure 2:
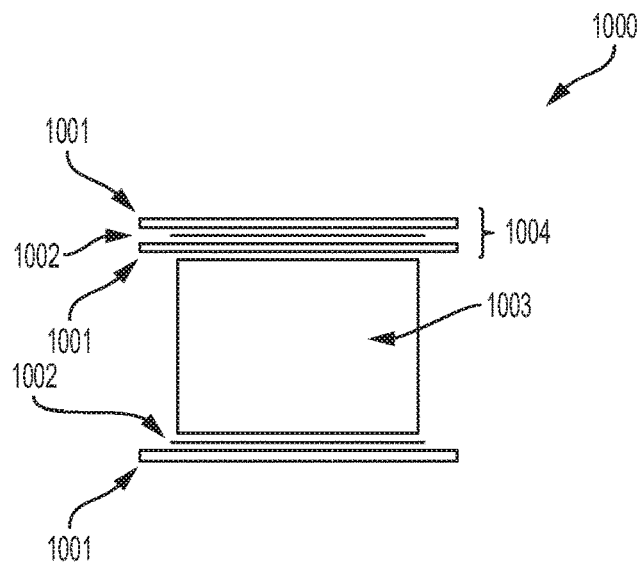
FIG. 2 is a cross-sectional view of an exemplary sample prepared for analysis by the exemplary prior art NMR-MOUSE shown in FIG. 1, the exemplary sample being disposable upon the sample surface of the NMR-MOUSE.
Figure 3:
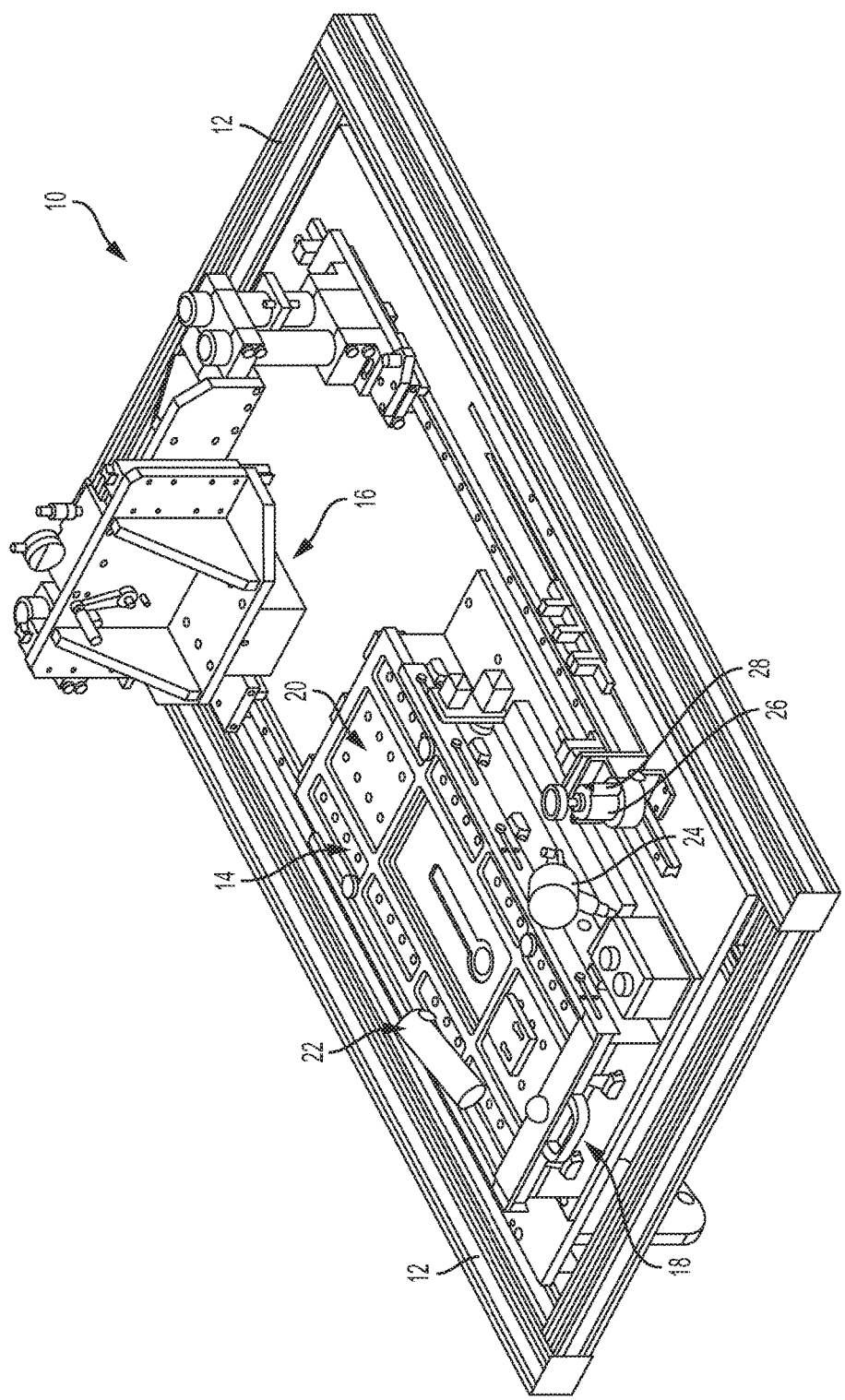
FIG. 3 is a perspective view of an exemplary device for the analysis of fluid distribution in absorbent articles in two and three dimensions consistent with the present disclosure.
Figure 4:
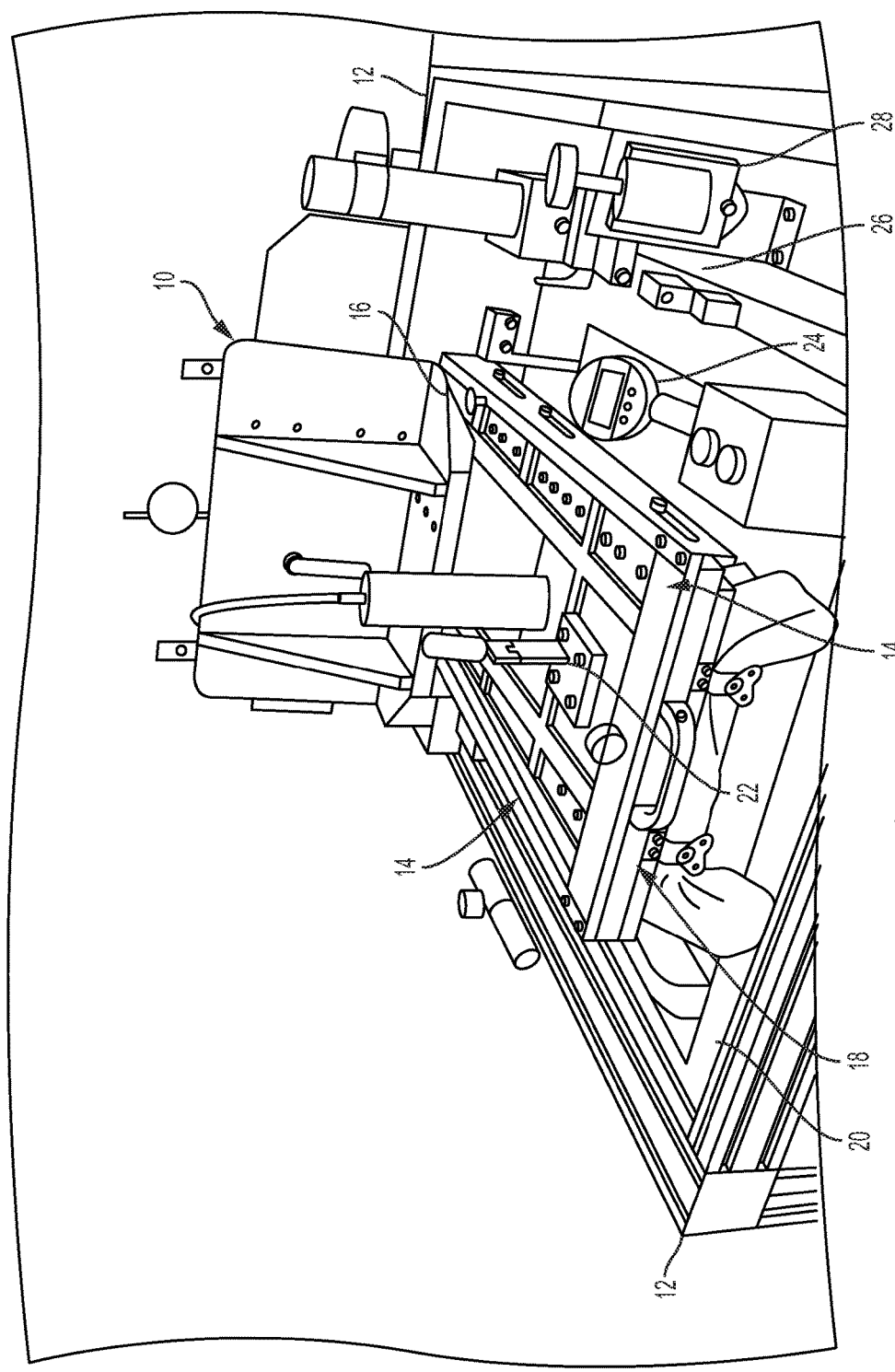
FIG. 4 is a photograph of an alternative perspective view of the exemplary device for the analysis of fluid distribution in absorbent articles in two and three dimensions of FIG. 3.

An exemplary, but non-limiting, embodiment of the improved device 10 for the analysis of the fluid distribution and kinetics in absorbent articles and any components thereof in at least two and preferably three dimensions is shown in FIGS. 3-4. The device 10 generally comprises a frame 12, a pressure chamber 14, and an NMR sensor 16. The pressure chamber 14 is generally formed from a conformable and pressurizable surface such as exemplary bladder assembly 18 and a top plate assembly 20 which includes a deposition assembly 22. It is believed that a conformable and pressurizable surface can provide a benefit in the application of a uniform pressure across a contoured surface, which is maintained even as the absorbent article is swelling non-uniformly during fluid acquisition and redistribution. Additionally, it is believed that a conformable and pressurizable surface can provide the ability to study fluid acquisition and redistribution under different amounts of pressure.

As used herein, the term "bladder assembly 18" is intended to include all forms of conformable surfaces reactive to a pressure applied thereto and should be construed in its broadest form to accommodate all forms of conformable surfaces suitable for the disposition of articles disposable between the conformable surface (e.g., exemplary bladder assembly 18, a conformable foam or gel, other pressurizeable structure and materials, and the like) and top plate assembly 20.

An exemplary, but non-limiting, bladder assembly 18 can be constructed of 12.7 mm Plexiglas to provide an overall dimension of 80 cm long by 30 cm wide by 5 cm tall. A manometer 24 can be provided for the measurement of the pressure inside the pressure chamber 14. A pressure gauge 26 can be provided to regulate the introduction of air into the pressure chamber 14 and can be positionably installed through access holes cooperatively disposed upon the right side of pressure chamber 14. One of skill in the art will understand that the manometer 24, a pressure gauge, and the pressure regulator 28 can be positioned anywhere upon pressure chamber 14 that provides efficacious positioning of the equipment as well as the ability to measure and/or adjust the pressures disposed within pressure chamber 14 as required by the end user.

Figure 5:
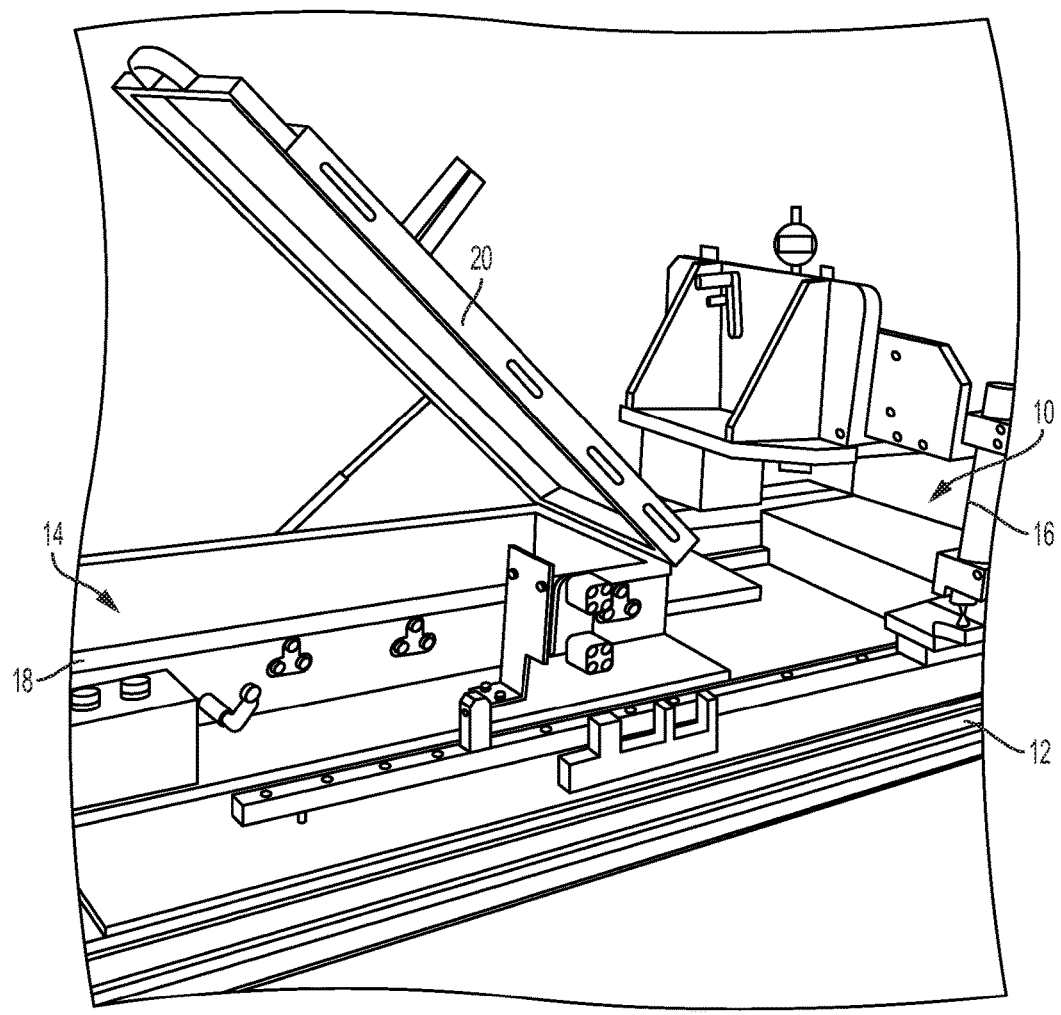
FIG. 5 is a photograph of an alternative perspective view of the exemplary device for the analysis of fluid distribution in absorbent articles in two and three dimensions of FIG. 3 where the top plate and bladder assembly of the pressure chamber are separated for sample insertion.

FIG. 5 provides an exemplary view of the device 10 showing the separable and displaceable nature of the top plate assembly 20 relative to the bladder assembly 18 of pressure chamber 14 as well as frame 12. As shown in the exemplary embodiment, the top plate assembly 20 can be attached to bladder assembly 18 and rotated about a longitudinal axis of attachment of top plate assembly 20 to the bladder assembly 18 at an angle, γ, to facilitate user access to that region of the internal portion of pressure chamber 14 disposed between top plate assembly 20 and bladder assembly 18. Alternatively, and as would be understood by one of skill in the art, top plate assembly 20 can be removeably attached to bladder assembly 18. This embodiment could facilitate the complete removal of top plate assembly 20 from bladder assembly 18 to allow a user access to the entire internal portion of pressure chamber 14 disposed between top plate assembly 20 and bladder assembly 18. A compression, hydraulic, pneumatic, or mechanical cylinder or other mechanism 30 can be used by one of skill in the art to secure top plate assembly 20 relative to bladder assembly 18 at a desired angle, γ, that facilitates user access to the internal portion of pressure chamber 14 disposed between top plate assembly 20 and bladder assembly 18.

Figure 6:
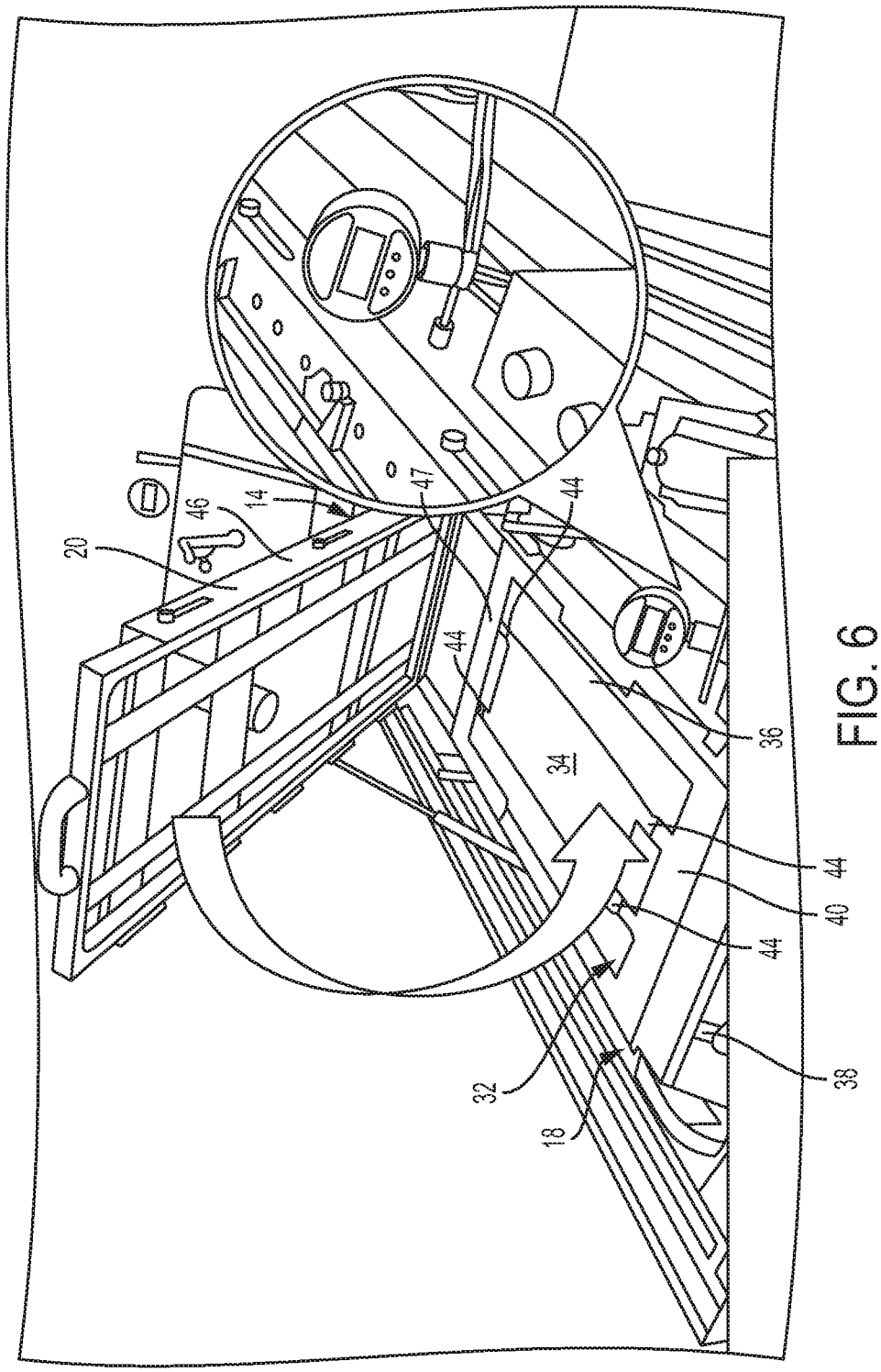
FIG. 6 is a photograph of yet another alternative perspective view of the exemplary device for the analysis of fluid distribution in absorbent articles in two and three dimensions of FIG. 3 where the top plate and bladder assembly of the pressure chamber are separated and a bladder and sample are inserted therein.

As shown in FIG. 6, the bladder assembly 18 of pressure chamber 14 can be provided with a bladder 32. Bladder 32 can be cooperatively associated and sealingly engaged to bladder assembly 18 of pressure chamber 14 by draping the bladder 32 over the top of bladder assembly 18 with sufficient slack to provide that the bladder 32 touches the bottom of bladder assembly 18 at its center point. An exemplary, but non-limiting, bladder 32 can be provided as a 50 mm×100 mm piece of silicone film having a thickness of 0.02 inches and a Shore A durometer value of 20. An exemplary material suitable for use as bladder 32 is available as Part#86435K85 from McMaster-Carr, Cleveland, Ohio.

Preferably, a secondary frame 36, having a fitting flange is fitted over the top of the bladder 32 and secured to the bladder assembly 18 with clamps 38. When bladder 32 is sealably secured to bladder assembly 32, it is preferred that the bladder 32/bladder assembly 32 combination assembly be leak free up to a pressure of 30 psi.

A front sample support 40 and back sample support 42 can be used to anchor a sample 34 or article to be measured by the device 10 relative to bladder assembly 18. As required, the sample 34 or article can attach to the front 40 and back 42 sample supports by attachment means 44. Such attachment can be provided by an end user as would be determined by one of skill in the art. Exemplary, but non-limiting, attachment means 44 can be provided as an adhesive tape fastening system, mechanical "hook" fasteners, adhesive attachment systems, combinations thereof, and the like. Front sample support 40 and back sample support 42 can be adjusted as may be required along the length (i.e., y-axis) of the secondary frame 36. The adjustment of front sample support 40 and back sample support relative to secondary frame 36 can be provided as a pin and hole system and the like as would be understood by one of skill in the art for the accommodation of differently sized absorbent articles to correctly align the loading point of the absorbent article.

The top plate assembly 20 can be provided by an appropriately sized Plexiglas® piece reinforced with a support frame 46 to enhance rigidity. It is preferred that the portion of top plate assembly 20 disposed proximate to the sample 34 that is disposed upon bladder 32 and proximate to the area that NMR sensor 16 will operate be essentially transparent to LF NMR radiation.

Figure 7:
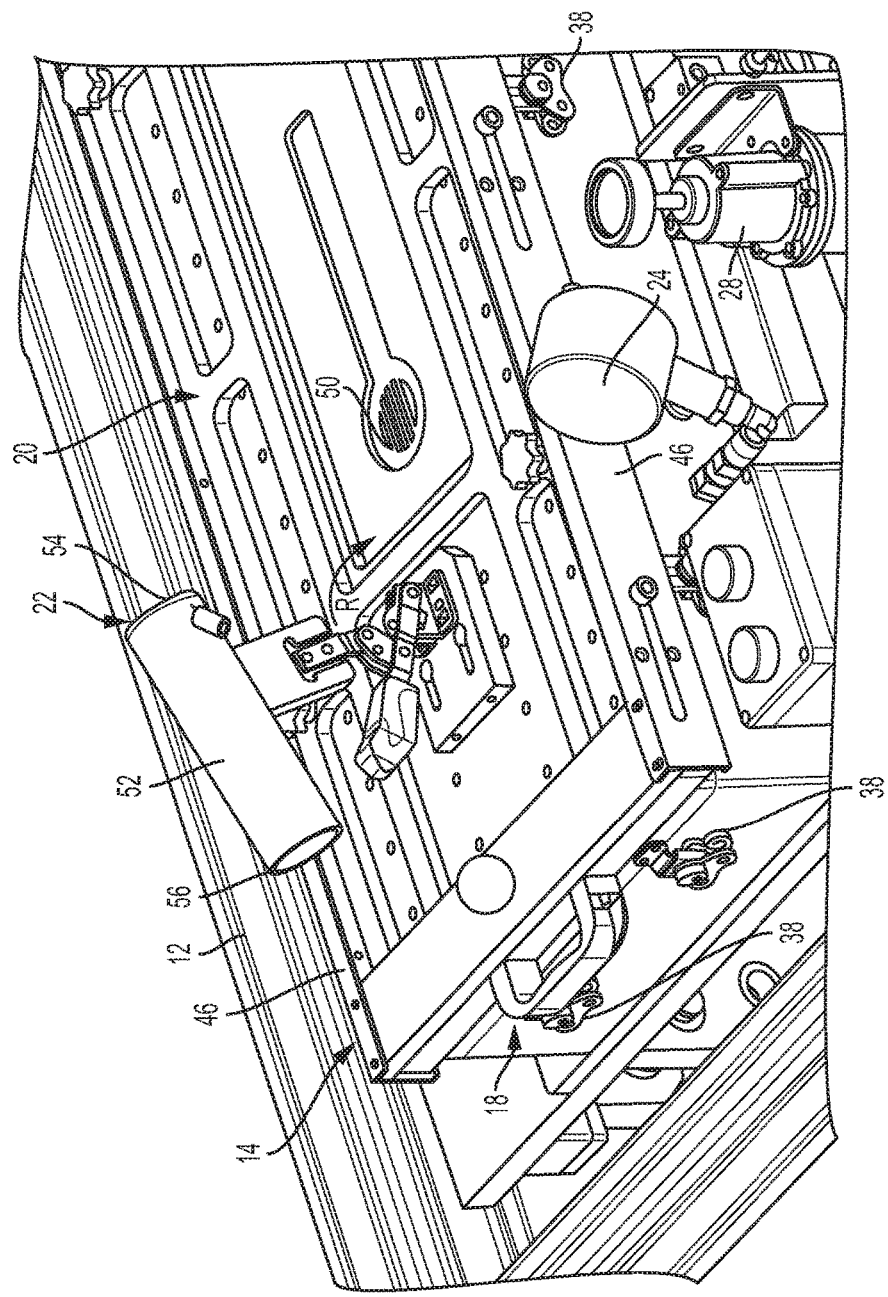
FIG. 7 is a perspective view of an exemplary deposition assembly suitable for cooperative engagement with the top plate of an exemplary pressure chamber.
Figure 8:
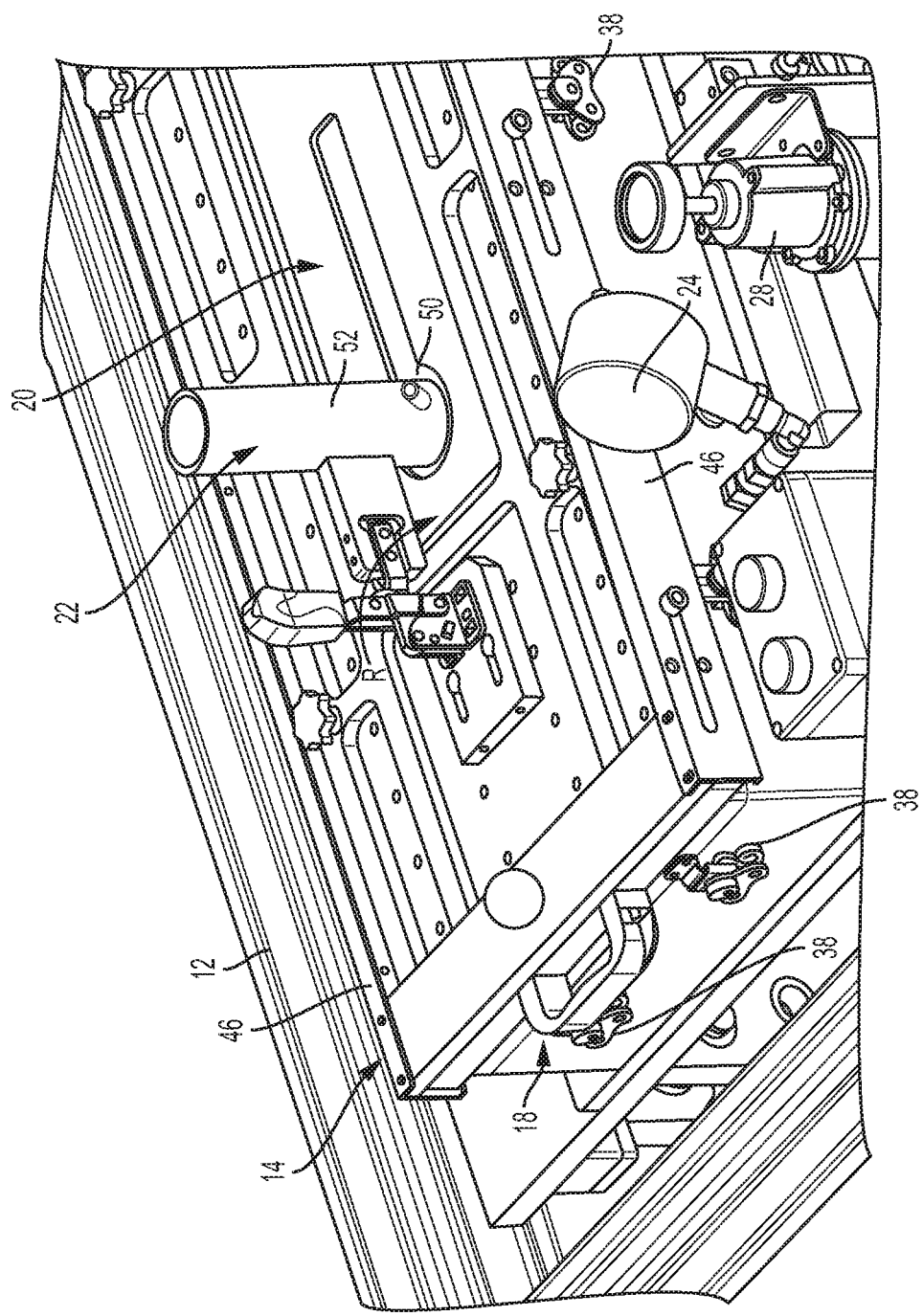
FIG. 8 is a perspective view of an exemplary deposition assembly in cooperative engagement with the insult application aperture disposed within the top plate of an exemplary pressure chamber.

As shown in FIGS. 7-8, an exemplary, but non-limiting, deposition assembly 22 can be disposed upon a surface of top plate assembly 20. Deposition assembly 22 can facilitate the deposition of an insult upon sample 34 disposed upon bladder 32 disposed within pressure chamber 14. Deposition assembly 22 is preferably rotatable about an axis, R, to facilitate the placement and displacement of deposition assembly into, and out of, contacting engagement with insult application aperture 50 disposed within top plate assembly 20. In a preferred embodiment, deposition assembly 22 is disposed so as to be located centrally relative to top plate assembly 20 and cooperatively aligned with insult application aperture 50.

One of skill in the art will appreciate that a suitable deposition assembly 22 can be constructed from a material that is transparent to NMR-level RF. An exemplary, but non-limiting material suitable for forming deposition assembly 22 can be constructed as a Plexiglas® cylinder 52. When deposition assembly 22 is cooperatively aligned with insult application aperture 50, it is preferred that deposition assembly 22 be inserted through the top plate assembly 20, through insult application aperture 50 so that the contacting edge 54 of deposition assembly 22 is cooperatively aligned with the surface of top plate assembly 20 that is in contacting engagement with sample 34 disposed within pressure chamber 14. A screen or mesh (e.g., a nylon screen, scrim material, and/or a perforated glass plate) can be affixed to contacting edge 54 of deposition assembly 22 to prevent the sample 34 from swelling into the cylinder 52. If desired, a cap (not shown) can be fitted upon non-contacting edge 56 cylinder 52 forming deposition assembly 22. A cap so applied to the non-contacting edge 56 cylinder 52 forming deposition assembly 22 can be provided with an aperture (not shown) to ensure that any negative pressure disposed within cylinder 52 forming deposition assembly 22 does not impede the absorption speed of an insult disposed upon sample 34.

One of skill in the art would be able to provide pressure-reducing apertures within top plate assembly 20. Such apertures can prevent air from being trapped under top plate assembly 20 as the bladder 32 is inflated but not to allow an insult applied to sample 34 through insult application aperture 50 to escape. One of skill in the art will appreciate that the device 10 is formed by the unique combination of a LF NMR sensor 16 in conjunction with the pressure chamber 14. An exemplary NMR sensor 16 can be provided as a single-sided NMR capable of producing depth profiles with microscopic spatial resolution. It would be recognized by one of skill in the art that an exemplary NMR sensor 16 can be provided with an open geometry that can provide a non-invasive and non-destructive testing method to characterize the depth structure of objects of arbitrary size. Such an exemplary NMR sensor 16 can provide a permanent magnet geometry that generates one plane of constant magnetic field intensity parallel to the scanner surface. A thin flat sensitive slice can be defined by combining the highly uniform static gradient with selective RF excitation. By moving the relative position between the slice and the object, one-dimensional profiles of the near surface of large samples can be produced with high spatial resolution.

An exemplary NMR sensor 16 can be provided with neodymium-iron-boron (NeFeB) magnets and an iron (Fe) yoke. An exemplary NMR sensor 16 can provide a magnetic field having a quadratic field behavior at the surface that becomes flat at a distance that depends on the gap, $G_s$, chosen between the magnets of NMR sensor 16. For example, the magnetic field at a distance of 15 mm from the surface and in the center of the NMR sensor 16 can be provided with a value of about 0.25 T and a strong uniform gradient of 11.2 T/m along the about the longitudinal axis of the array of magnets. This can define a plane of constant field intensity parallel to the surface with a field variation smaller than 0.1 mT along the longitudinal axis. This can be achieved by choosing a RF coil having suitable dimensions.

The RF coil and tuning circuit used in combination with the magnet should generally satisfy a number of needs. First, the dimension of the coil can be determined by the lateral dimensions of the sensitive region where the magnet system defines a flat slice. Second, the coil should have a low inductance in order to reduce any detuning generated during the scanning procedure. This can involve movement of the sensor with respect to the sample to be analyzed and can change the load of the coil. Third, the maximum depth desired can determine the distance at which the coil should be positioned away from the magnet surface.

A preferred RF coil used to fulfill these requirements can be provided as a two-turn rectangular coil wound with copper wire. A parallel tank-circuit can be used for tuning and matching of the RF coil. An exemplary 10.6 MHz L-C tank circuit suitable for tuning the RF coil can be assembled with a low inductance of about 0.12 pH and 2000 pF. This L-C tank circuit can provide a nominal circuit quality factor, Q factor, of 65 which leads to a dead time of about 25 µsec. By introducing a resistance in parallel to the coil, the Q factor of the L-C tank circuit can be reduced to lower the dead time. For example, a coil having an overall resistance of 270Ω can reduce the L-C tank circuit Q factor to 18 providing an exemplary dead time of about 7 pec.

An exemplary NMR sensor 16 can also incorporate a system to adjust the position of the magnet forming the magnet array of NMR sensor 16 relative to a sample disposed thereupon. For example, a mechanical lift device can position the magnet array of NMR sensor 16 at a desired distance relative to the sample 34. The position of the magnets associated with the NMR sensor 16 can be controlled by a high-precision screw controlled by a stepper-motor as would be recognized by one of skill in the art.

Accordingly, the NMR sensor 16 is preferably arranged to generate a sufficiently homogeneous magnetic field over a volume, $V_a$, located at a location along the z-axis in the sample 34 thereby causing excitation of subject nuclei in the volume $V_a$, and to detect radio frequency emissions from the subject nuclei in the volume $V_a$ by using an optimized CPMG pulse sequence. The apparatus is preferably arranged to, substantially immediately following excitation of volume $V_a$, cause excitation of subject nuclei in a volume, $V_b$, where $V_b$ is a volume differing from $V_a$ only in its position along the longitudinal axis, and to detect radio frequency emissions from the subject nuclei in the volume $V_b$.

In an exemplary embodiment, the quantification of liquids in a sample 34 (such as absorbent hygiene materials and products), an optimized CPMG pulse sequence in combination with the use of a suitable contrast agent can make the $T_1$ and $T_2$ times independent of the sample 34 (and the parts thereof) and the sample 34 saturation levels that can enable the fast quantification of liquids inside the sample 34. In a preferred embodiment, the NMR sensor 16 can be provided with an optimized CPMG pulse sequence (discussed supra) having a 90° x-pulse followed by a refocusing pulse of 180° y-pulse.

Such an optimized CPMG pulse sequence can allow for the collection of NMR Amplitude data (in arbitrary units, a.u.) versus depth (in µm) as the high precision lift of NMR sensor 16 sequentially steps through the sample 34 depth and to measure the kinetics of a fluid disposed within a defined volume disposed inside the sample 34:

To enable the quantification of liquids using below mentioned parameters the $T_1$ relaxation time should be below 50 ms and a $T_2 > 20$ ms. An exemplary NMR sensor having a gradient of 8 T/m, a measuring frequency of 13.5 MHz, and a quadratic surface coil with dimension of 40 mm can be used to excite a sensitive slice with a certain thickness, which is proportional to the bandwidth of the RF-pulse according to the following equation:

$$\Delta z = 2\pi \Delta v / G_z \gamma$$

Where, $\Delta v$ is bandwidth, $G_z$ is gradient and $\gamma$ is the gyromagnetic ratio. In the CPMG sequence the thickness of sensitive slice could be adjusted with number of acquisition points (m) in each echo and dwell time (dw) where the acquisition window s:

m·dw

Furthermore, the thickness of the sensitive slice should be the same as measuring step size.

Repetition Time=200 ms
90° Amplitude=−7 dB
180° Amplitude=0 dB
Pulse Length=5 µs
Echo Time=90 µs
Number of Echoes for kinetics=128
Number of Echoes for profiling=8
Echo Shift=1 µs
Rx Gain=31 dB
Number of Scans for kinetics=1
Number of Scans for profiling=8

Rx Phase can be determined during the phase adjustment. It was surprisingly found that a value of 230° was acceptable. It was also surprisingly found that pulse length can depend on measurement depth which can be adjusted as required.

Figure 9:
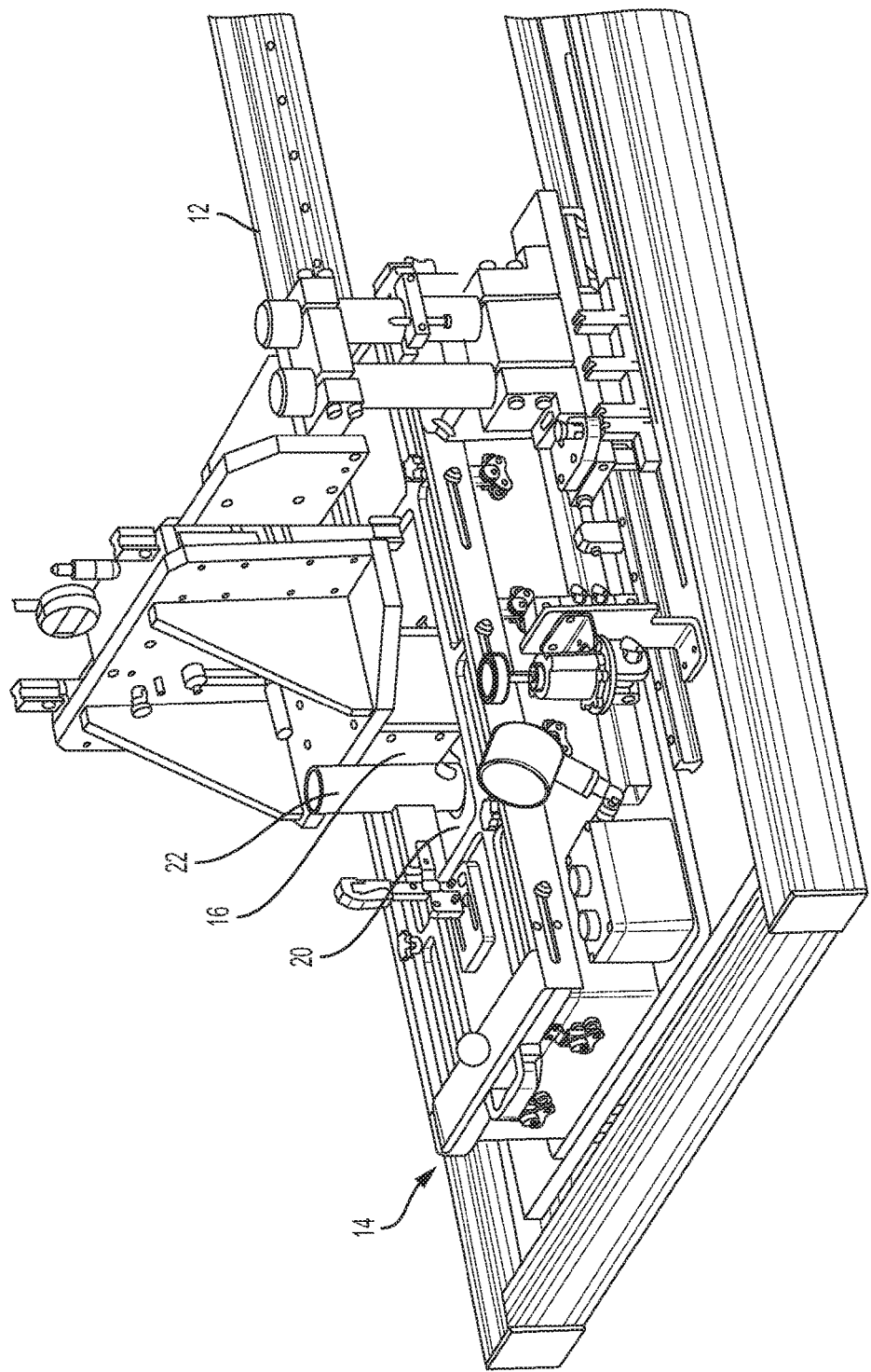
FIG. 9 is a perspective view of a device for the analysis of fluid distribution in absorbent articles in two and three dimensions where the NMR sensor is disposed proximate to a sample disposed within the pressure chamber.
Figure 10:
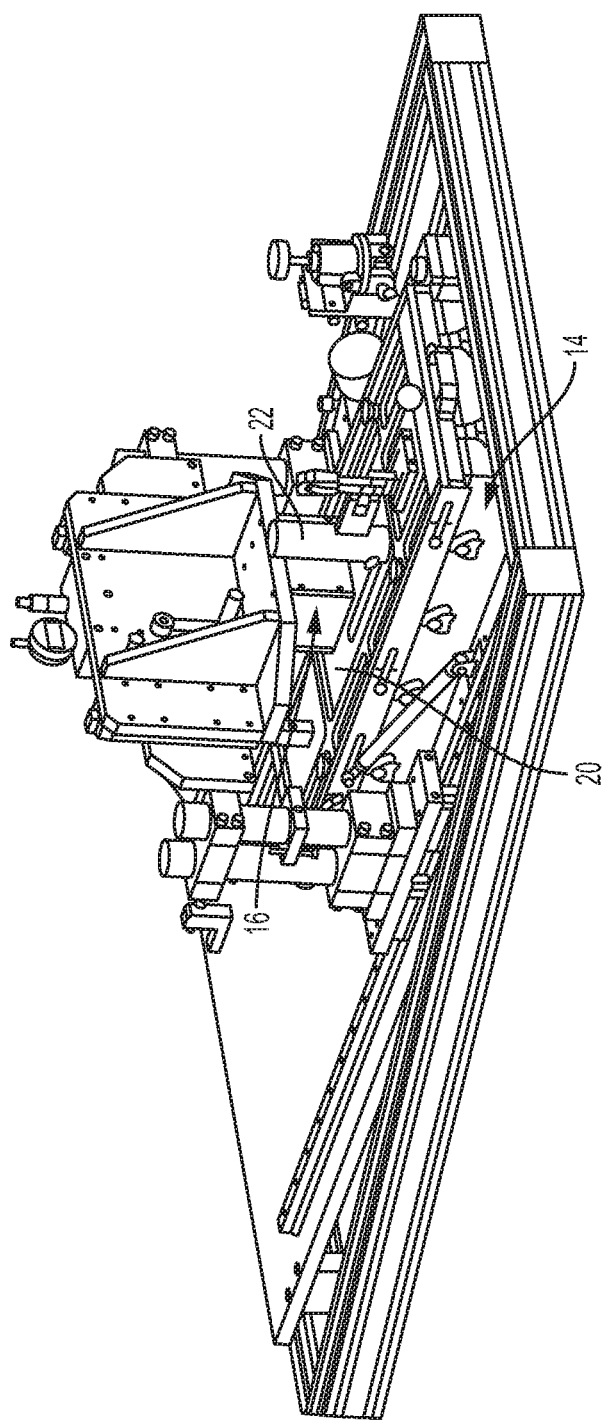
FIG. 10 is an alternative perspective view of the device for the analysis of fluid distribution in absorbent articles in two and three dimensions of FIG. 9 where the NMR sensor is disposed proximate to a sample disposed within the pressure chamber.
Figure 11:
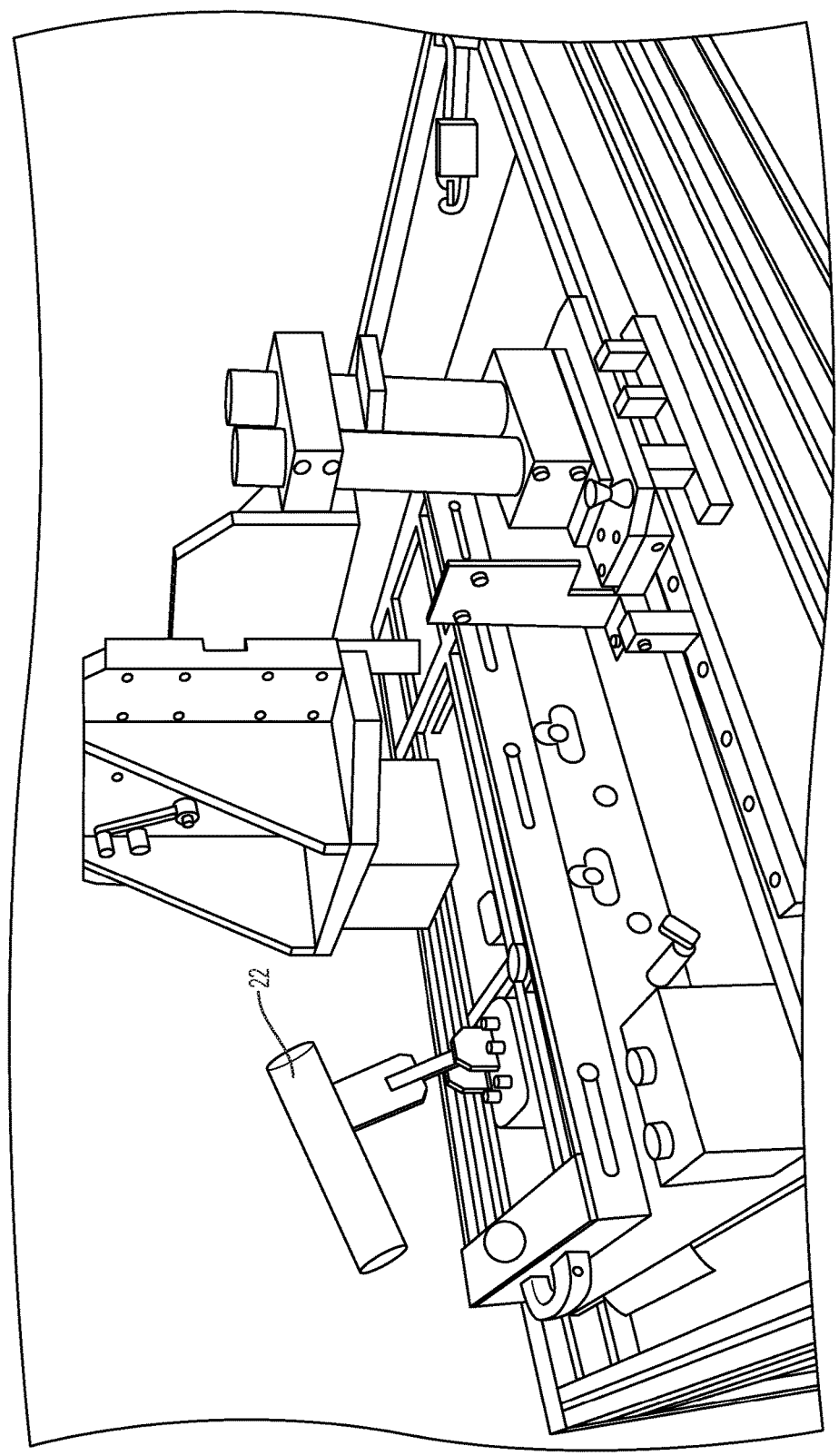
FIG. 11 is a photograph of the device for the analysis of fluid distribution in absorbent articles in two and three dimensions of FIG. 9 where the NMR sensor is disposed proximate to a sample disposed within the pressure chamber.

Referring to FIGS. 9-11 an exemplary NMR sensor 16 (a suitable exemplary, but non-limiting, NMR sensor 16 being described supra) is provided proximate to, and in cooperative engagement with, the frame and top plate assembly 20 of pressure chamber 14. It is preferred that NMR sensor 16 be positioned in a manner so that magnetic gradient developed by NMR sensor 16 is directed toward sample 34 disposed between the top plate assembly 20 and the bladder assembly 18 of pressure chamber 14. When provided in this configuration, NMR sensor 16 can excite a portion inside the sample 34 (e.g., known in the art as a "sensitive slice") and monitor the radio frequency emissions from the subject nuclei of sample 34 disposed within the overall magnetic volume and/or within selected regions of the overall magnetic volume created by NMR sensor 16 as an insult that is applied to the top surface of sample 34 migrates into sample 34.

It is believed that device 10 can facilitate the measurement of liquid dynamics and liquid distribution quantitatively in swelling and non-swelling samples 34. One of skill in the art will understand that this is because the distance between the NMR sensor 16 and the top layer of the sample disposed within pressure chamber 14 (as discussed supra)

remains constant during swelling of the sample 34 (i.e., the field-of-view, FOV, will be independent of sample 34 swelling) as absorption of the insult applied to the sample 34 occurs.

Figure 12:
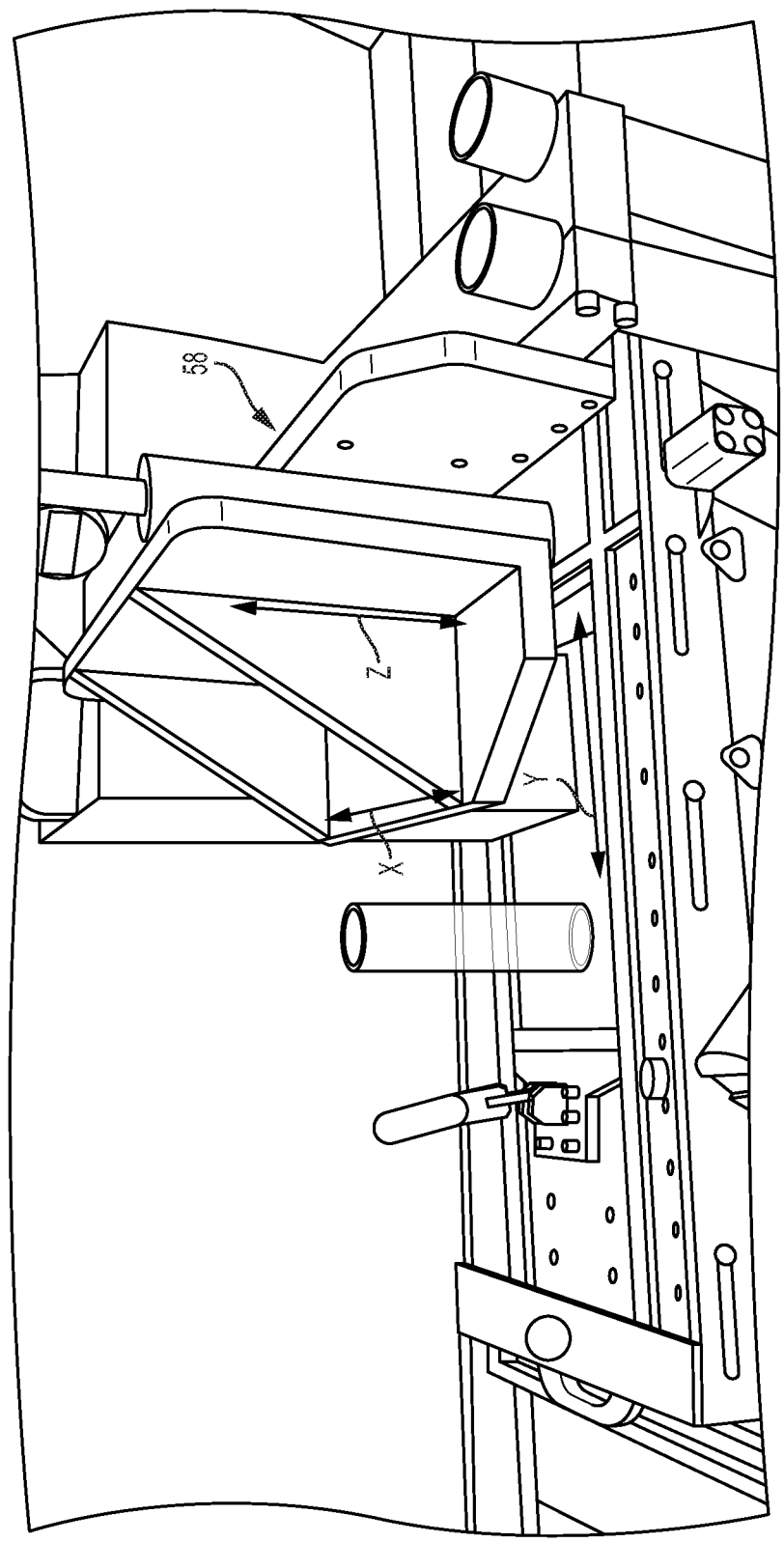
FIG. 12 is a photograph of the device for the analysis of fluid distribution in absorbent articles in two and three dimensions of FIG. 9 where the NMR sensor is translatable relative to a sample disposed within the pressure chamber.
Figure 13:
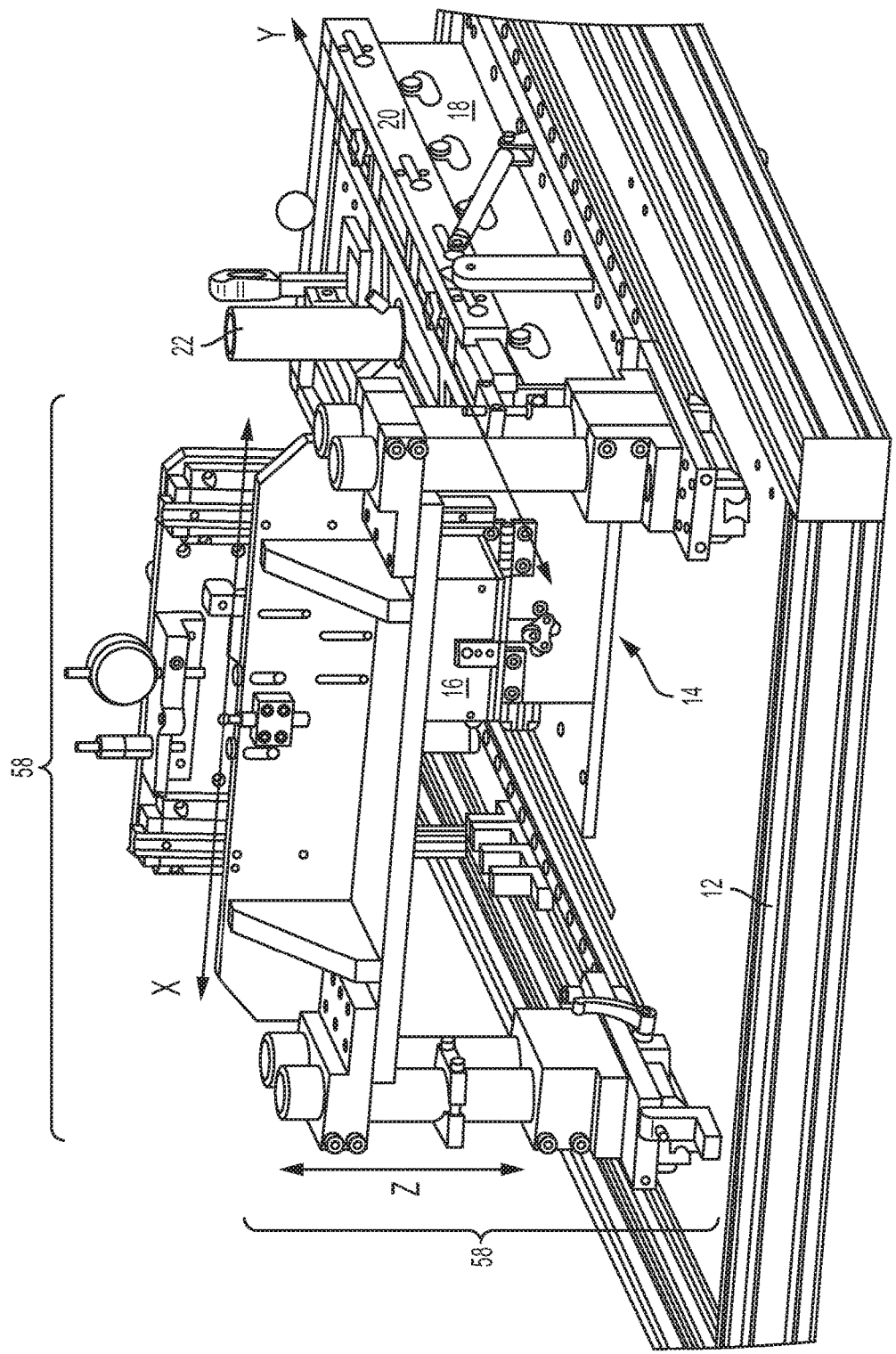
FIG. 13 is a perspective view of the device for the analysis of fluid distribution in absorbent articles in two and three dimensions of FIG. 9 where the NMR sensor is translatable relative to a sample disposed within the pressure chamber.

As shown in FIGS. 10 and 12-13, NMR sensor 16 can be cooperatively associated with pressure chamber 14 to provide NMR sensor 16 with at least 2- and preferably 3-axis movement (i.e., x, y, and z) relative to frame 12, pressure chamber 14, and any sample 34 disposed within pressure chamber 14. Such movement of the NMR sensor 16 can be provided to influence the constant distance of the NMR sensor 16 relative to the surface of sample 34 during the introduction of any insult thereto.

By way of non-limiting embodiment, 3-axis movement can be provided for NMR sensor 16 by a positioning plate 58 that is cooperatively attached to, and engaged with, NMR sensor 16. Positioning plate 58 can provide a desired longitudinal movement (i.e., MD or y-axis) of the NMR sensor 16 relative to pressure chamber 14 and a sample 34 disposed therein, a desired lateral movement (i.e., CD or x-axis) of the NMR sensor 16 relative to pressure chamber 14 and a sample 34 disposed therein, and/or a desired vertical movement (i.e., Z-direction or z-axis) of the NMR sensor 16 relative to pressure chamber 14 and a sample 34 disposed therein.

The ability of positioning plate 58 to manipulate the movement of the NMR sensor 16 relative to pressure chamber 14 and a sample 34 disposed therein can be provided as would be done by one of skill in the art in translational and/or positional mechanics. By way of non-limiting examples, a translational movement of NMR sensor 16 relative to pressure chamber 14 and a sample 34 disposed therein can be provided by a cam/cam follower system, mechanical actuators, hydraulic actuators, pneumatic actuators, piezoelectric actuators, electro-mechanical actuators, linear motors, telescoping linear actuator, combinations thereof, and the like. In any regard, the method of providing translational movement to NMR sensor 16 through the use of positioning plate 58 can be selected by the end user of device 10 to provide the relevant degree of accuracy in order to accomplish the measurement required by device 10.

Figure 14:
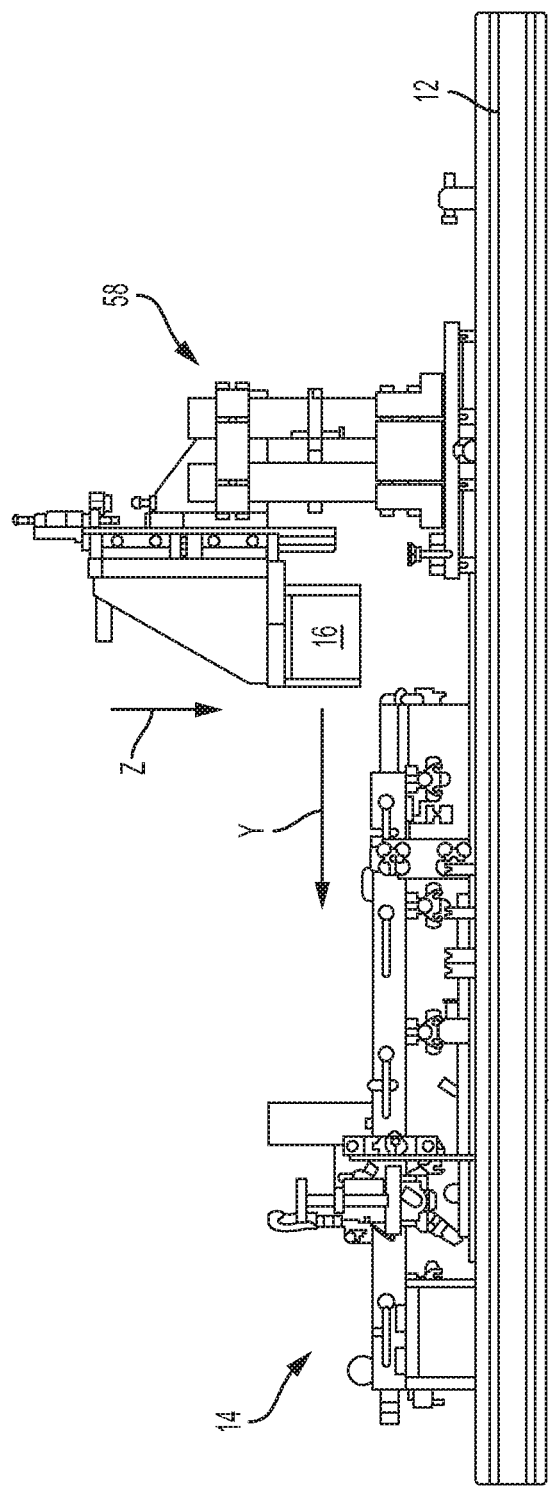
FIG. 14 is a plan view of the device for the analysis of fluid distribution in absorbent articles in two and three dimensions of FIG. 9 where the NMR sensor is translated away from a sample disposed within the pressure chamber.
Figure 15:
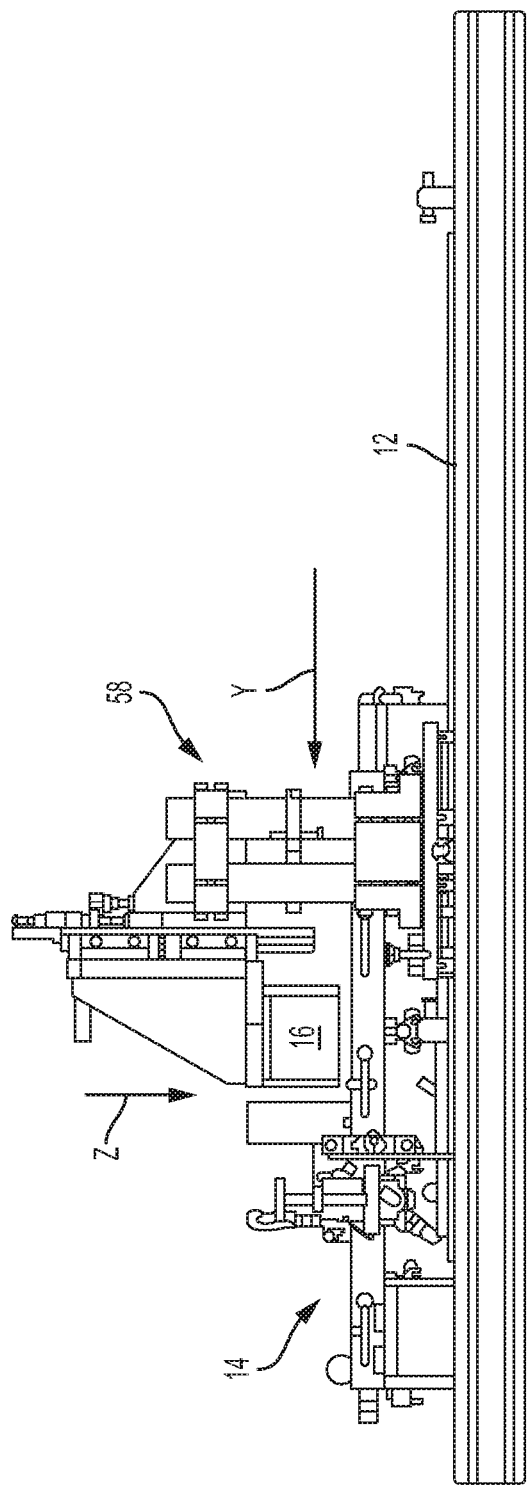
FIG. 15 is a plan view of the device for measuring fluid distribution in absorbent articles in two and three dimensions of FIG. 9 where the NMR sensor is translated proximate to a sample disposed within the pressure chamber.

Exemplary FIGS. 14-15 show the translation of NMR sensor 16 relative to frame 12, pressure chamber 14, and a sample 34 disposed within pressure chamber 14, relative to the y-axis (MD) and the z-axis (Z-direction). The advantages provided by the ability of NMR sensor 16 to translate relative to any of frame 12, pressure chamber 14, and/or sample 34 disposed within pressure chamber 14 relative to the y-axis (MD), x-axis (CD) and/or z-axis (Z-direction) would be readily recognized by one of skill in the art as providing the ability to analyze every point of sample 34 in situ. Such in situ measurements at every point of sample 34 can assist in understanding the fluid dynamics associated with the flow of a fluid within and throughout sample 34 which is instituted as an insult to the surface of sample 34 by allowing NMR sensor 34 to relocate to a desired position relative to sample 34 and observe the progress of the fluid within the sample in real-time or near real-time and provide heretofore unseen accuracy in the effort to model such fluid flow through an article 34.

Additionally, one of skill in the art will appreciate the value and advantage of providing both pressure chamber 14 and NMR sensor 16 with axial (e.g., radial) movement relative to frame 12. Without desiring to be bound by theory, it is believed that such movement of pressure chamber 14 and NMR sensor 16 relative to frame 12 can allow for the measurement of a liquid distribution in relative to any combination of the x- (CD), y- (MD), and/or z-axis (Z-direction) and as a function of the inclined product. It is believed that such 3-directional movement of the pressure chamber 14 and NMR sensor 16 relative to frame 12 can effectively simulate the flow of an insult applied to a sample 34 worn by a user.

Figure 16:
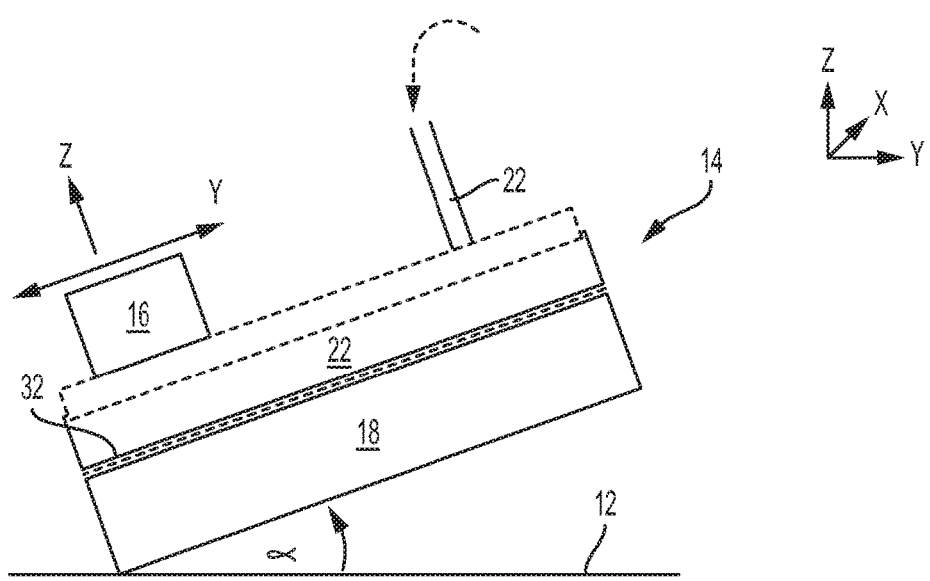
FIG. 16 is a plan view of a device for the analysis of fluid distribution in absorbent articles in two and three dimensions where the NMR sensor and pressure chamber are translated axially in the y-direction (MD) relative to the frame.
Figure 17:
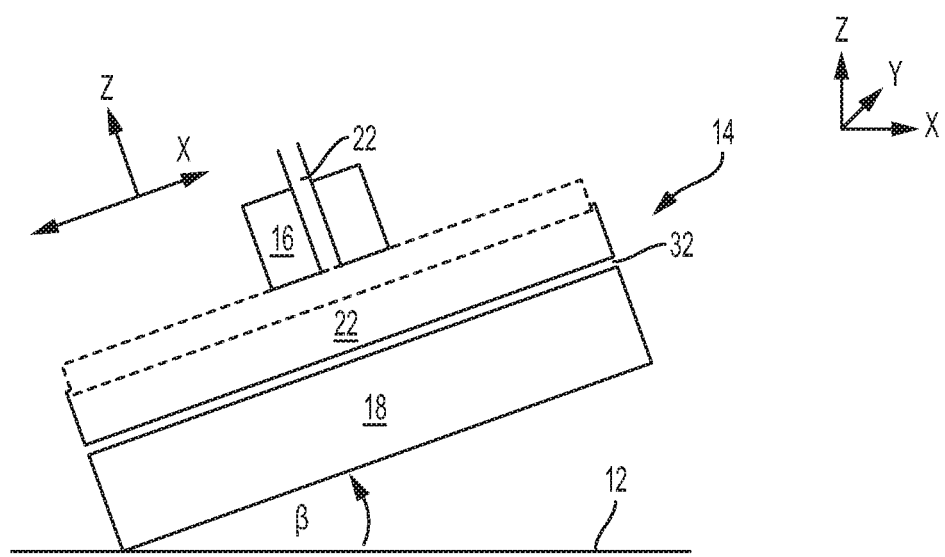
FIG. 17 is a plan view of a device for the analysis of fluid distribution in absorbent articles in two and three dimensions where the NMR sensor and pressure chamber are translated axially in the x-direction (CD) relative to the frame; and, FIG. 18 is a perspective view of an exemplary rotation mechanism suitable for providing x-, y-, and z-axis rotation of the NMR sensor and pressure chamber relative to the frame.

By way of non-limiting example, FIGS. 16-17 show the ability of the combined and cooperatively associated and engaged NMR sensor 16 and pressure chamber 14 to be rotated in any of the x- (CD), y- (MD), and/or z-axis (Z-direction) relative to frame 12. By way of non-limiting example, and as shown in FIG. 16, the combined NMR sensor 16 and pressure chamber 14 can be rotated about the x-axis relative to frame 12 through an angle, α. As shown in FIG. 17, the combined NMR sensor 16 and pressure chamber 14 can be rotated about the y-axis relative to frame 12 through an angle, β. Clearly, one of skill in the art would be able to understand and provide for the combined NMR sensor 16 and pressure chamber 14 can be rotated about both the x-axis and y-axis relative to frame 12 through a combination of angle α and angle β.

It is believed that providing the ability of the combined NMR sensor 16 and pressure chamber 14 to be rotated about any of the x-axis and y-axis relative to frame 12 can effectively provide a sample 34 disposed within pressure chamber 14 with an angle relative to the horizon that could more accurately simulate a real-life situation where the sample 34 is worn by a user and the user has assumed a reclined (or any other-than-standing) position. One of skill in the art will readily appreciate that sample 34 in the form of an absorbent article such as a diaper or a catamenial device, once applied to a human form, rarely maintains a completely flat, planar, horizontal orientation. Such an absorbent article will assume a form that conforms to the wearer and will have regions that have varying orientations relative to the horizon. Thus, one of skill in the art will appreciate the ability of the combined NMR sensor 16 and pressure chamber 14 that is adapted to be rotated relative to frame 12 can now provide the curious analyst with a more real-world analysis of fluid flow through an absorbent article by more accurately simulating, and the ability to now model, a real world wearing of the absorbent article. This ability has not been realized by any known NMR fluid flow analytical analysis and/or modeling system.

Figure 18:
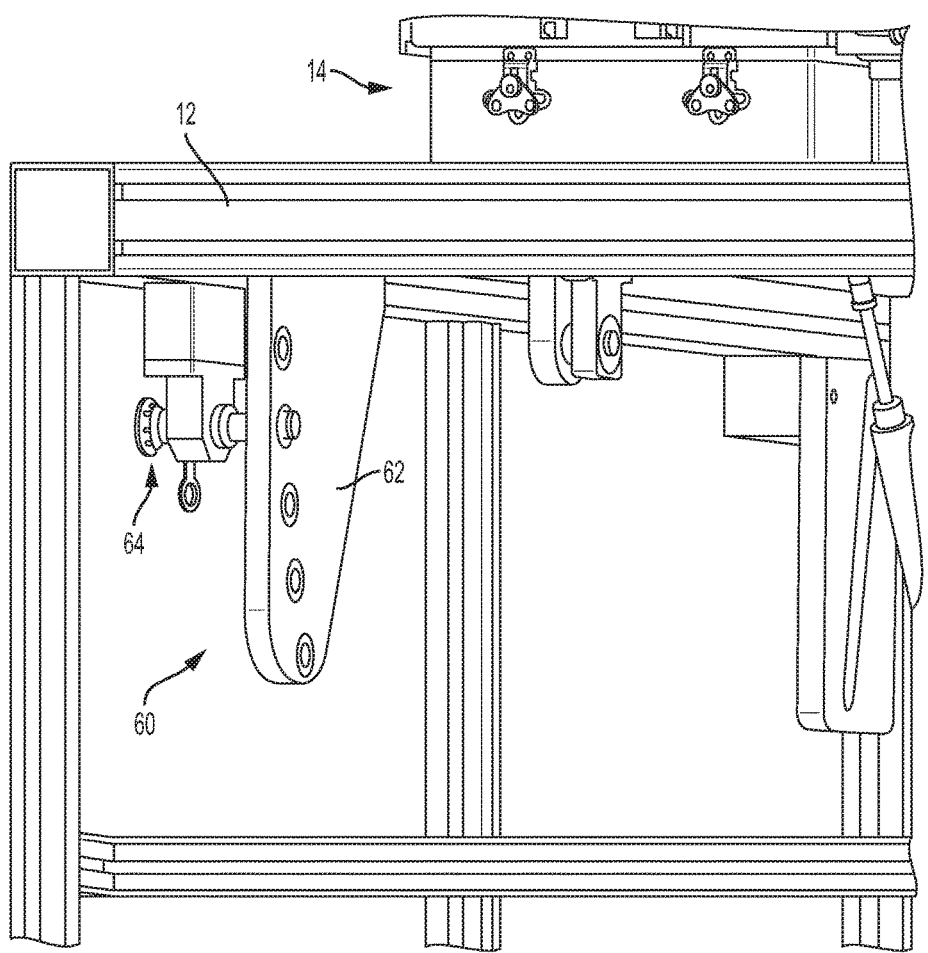

Providing the ability of the combined NMR sensor 16 and pressure chamber 14 to be rotated about any of the x-axis and y-axis relative to frame 12 can be accomplished by any means known to those of skill in the mechanical arts. By way of non-limiting example, FIG. 18 provides for a rotation mechanism 60 having a pin 64 and hole system 62. As would be recognized by one of skill in the art, the pin 64 can be removed from a corresponding first hole disposed within hole system 62. The combined NMR sensor 16 and pressure chamber 14 can then be rotated about any of the x- and/or y-axis and the pin 64 can be engaged with a second hole disposed within hole system 62. Naturally, one of skill in the art could utilize any number of positioning systems suitable for re-orienting the combined NMR sensor 16 and pressure chamber 14 relative to frame 12. Suitable positioning systems can be provided by any suitable mechanical actuators, hydraulic actuators, pneumatic actuators, piezoelectric actuators, electro-mechanical actuators, linear motors, telescoping linear actuator, combinations thereof, and the like.

The disclosed device can, for the first time, allow the end-user to quantify liquid volumes and migration inside absorbent articles at low cost. A huge benefit versus currently used acquisition test methods in the absorbent article manufacturing industry is that here with a low cost benchtop system, the endpoint detection of liquid absorption has been shifted from the product surface into the product which dramatically changes innovation. It allows for the first time, a fast screening of liquid flow and distribution inside hygiene materials and products to guide development, IP, claim support and any required user-defined sample modeling.

For example, the use of device 10 can hold an absorbent article under a constant pressure from the bottom. This can allow the absorbent article to swell toward the bottom during the application of the insult to the top. Further, the device 10 can facilitate the measurement of liquid kinetics at the point where the insult is introduced to the absorbent article surface at a given or desired pressure.

All publications, patent applications, and issued patents mentioned herein are hereby incorporated in their entirety by reference. Citation of any reference is not an admission regarding any determination as to its availability as prior art to the claimed invention.

This application claims the benefit of U.S. Provisional Application No. 62/408,114 filed on Oct. 14, 2016, the entirety of which is incorporated by reference herein.

The dimensions and/or values disclosed herein are not to be understood as being strictly limited to the exact numerical values recited. Instead, unless otherwise specified, each such dimension and/or value is intended to mean both the recited dimension and/or value and a functionally equivalent range surrounding that dimension and/or value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A device for the analysis of fluid distribution in an absorbent article, the device comprising:
   a. a frame;
   b. a pressure chamber disposed in contacting and mating engagement with said frame, said pressure chamber comprising a top plate and a bladder, said absorbent article being disposed between said top plate and said bladder;
   c. a NMR sensor in cooperative engagement with said frame and said pressure chamber, said NMR sensor being disposed proximate to said pressure chamber, said NMR sensor measuring said fluid distribution in said absorbent article when said absorbent article is disposed between said top plate and said bladder of said pressure chamber and said NMR sensor is disposed proximate to a surface of said absorbent article; and
   d. a deposition assembly, said deposition assembly providing an insult to a surface of said absorbent article disposed proximate to said NMR sensor when said absorbent article is disposed between said top plate and said bladder.

2. The device of claim 1 wherein said top plate of said pressure chamber further comprises an insult application aperture, said insult application aperture providing contacting engagement of said insult from said deposition assembly with said surface of said absorbent article disposed proximate to said NMR sensor.

3. The device of claim 1 wherein said NMR sensor is translatable from a first position wherein said NMR sensor is not disposed proximate to said absorbent article to a second position disposed proximate to said absorbent article.

4. The device of claim 3 wherein said NMR sensor is translatable from said second position proximate to said absorbent article to a third position proximate to absorbent article.

5. The device of claim 4 wherein said NMR sensor measures a first fluid distribution in said absorbent article at said first position and said NMR sensor measures a second fluid distribution in said absorbent article at said second position after said NMR sensor translates to said second position from said first position.

6. The device of claim 1 further comprising support frame, said support frame being disposed within said pressure chamber, said frame providing attachment means for attaching said absorbent article thereto.

7. The device of claim 6 wherein said absorbent article is attached to said frame and disposed between said bladder and said top plate of said pressure chamber.

* * * * *